US006271445B1

United States Patent
Ward et al.

(12) United States Patent
(10) Patent No.: US 6,271,445 B1
(45) Date of Patent: Aug. 7, 2001

(54) NUCLEIC ACID MOLECULES ENCODING 5'-PHOSPHORIBOSYL-5-AMINOIMIDAZOLE (AIR) SYNTHETASE

(75) Inventors: Eric Russell Ward; David Charles Guyer, both of Durham; Sharon Lee Potter, Raleigh, all of NC (US); Venkiteswaran Subramanian, Danville; Eric Walters, Scotts Valley, both of CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/338,420

(22) Filed: Jun. 22, 1999

Related U.S. Application Data

(60) Provisional application No. 60/155,234, filed on Jun. 24, 1998, now abandoned.

(51) Int. Cl.[7] .................... C12N 15/29; C12N 15/82; C12N 5/14; A01H 5/00; A01H 5/10
(52) U.S. Cl. ............... 800/300; 536/23.6; 435/252.3; 435/320.1; 435/419
(58) Field of Search ................ 435/252.3, 468, 435/183, 410, 320.1, 418, 419, 69.1; 536/23.2, 23.6; 800/278, 300, 295, 298; 47/58.1

(56) References Cited

PUBLICATIONS

Senecoff et al. De Novo purine synthesis in Arabidopsis thaliana. Plant Physiology 112:905–917, 1996.*
Senecoff et al. Isolating the Arabidopsis thaliana genes for de Novo purine synthesis by suppression of Escherichia coli mutants. Plant Physiology 102:387–399, 1993.*
Yuan et al. Modification of plant components. Current Opinion in Biotechnology 8:227–233, 1997.*
Abell et al., "Biochemical approaches to herbicide discovery: advances in enzyme target identification and inhibitor design", Weed Science, US, 44: 734–742 (1996).
Schrimsher et al.,Isolation of a Multifunctional Protein with Aminoimidazole Ribonucleotide Synthetase, Glycinamide Ribonucleotide Synthetase, and Glycinamide, Ribonucleotide Transformylase Activities: Characterization of Aminoimidazole Ribonucleotide Synthetase, Biochemistry, 25:4356–4365 (1986).
Stemmer, Willem P.C., Rapid evolution of a protein in vitro by DNA shuffling, Nature, 370:389–391 (1994).
Bratton et al., "A New Coupling Component for Sulfanilamide Determination," J. Biol. Chem., 128:537–550 (1939).
Houlberg et al., "Identification of the Enzymatic Reactions Encoded by the purG and purI Genes of Escherichia coli," Journal of Bacteriology, 154(3): 1485–1488 (1983).
Schnorr et al., "Molecular characterization of Arabidopsis thaliana cDNAs encoding three purine biosynthetic enzymes," The Plant Journal, 6(1): 113–121 (1994).
Schrimsher et al., "Isolation of a Multifunctional Protein with Aminoimidazole Ribonucleotide Synthetase, Glycinamide Ribonucleotide Synthetase, and Glycinamide Ribonucleotide Transformylase: Characterization of Aminoimidazole Ribonucleotide Synthetase," Biochemistry, 25(15):4356–4365 (1986).
Schrimsher et al., "Purification and Characterization of Aminoimidazole Ribonucleotide Synthetase from Escherichia coli," Biochemistry, 25: 4366–4371 (1986).
Senecoff et al., "Isolating the Arabidopsis thaliana Genes for de Novo Purine Synthesis by Suppression of Escherichia coli Mutants," Plant Physiol., 102: 387–399 (1993),

* cited by examiner

*Primary Examiner*—Amy Nelson
*Assistant Examiner*—David H Kruse
(74) *Attorney, Agent, or Firm*—Edouard G. Lebel; Larry W. Stults; J. Timothy Meigs

(57) ABSTRACT

The present invention discloses plant derived nucleic acid molecules and proteins. The protein disclosed in the present invention have 5'-phosphoribosyl-5-aminoimidazole (AIR) synthetase activity. Furthermore, the present invention provides methods for producing transgenic plants, transgenic plant tissues, transgenic plant seeds, and transgenick plant cells using genes encoding enzymes having AIR synthetase activity.

21 Claims, No Drawings

NUCLEIC ACID MOLECULES ENCODING 5'-PHOSPHORIBOSYL-5-AMINOIMIDAZOLE (AIR) SYNTHETASE

This application claims the benefit of U.S. Provisional Application No. 60/155,234, filed May 24, 1998 now abandoned.

FIELD OF THE INVENTION

The invention relates to methods for screening herbicidal compounds which inhibit the enzymatic activity of 5'-phosphoribosyl-5-aminoimidazole (AIR) synthetase, an enzyme involved in de novo purine biosynthesis. The invention also relates to the use of thereby identified herbicidal chemicals to control the growth of undesired vegetation. The invention may also be applied to the development of herbicide tolerance in plants, plant tissues, plant seeds, and plant cells.

BACKGROUND OF THE INVENTION

I. AIR Synthetase

The AIR synthetase is an enzymatic step in the de novo purine biosynthesis pathway, which leads to the synthesis of the purine nucleotides IMP, AMP and GMP. De novo purine biosynthesis plays a central role in the nitrogen assimilation pathway and is conserved among bacteria, yeast, Drosophila and mammals (Schnorr et al. (1994) The Plant Journal, 6: 113–121). The AIR synthetase enzymatic activity corresponds to the fifth step in the pathway and catalyzes the conversion of 5'-phosphoribosyl-N-formylglycinamidine (FGAM) to 5'-phosphoribosyl-5-aminoimidazole (AIR). In *E. coli*, this step is carried out by a protein encoded by the purM gene. Recently, an Arabidopsis c-DNA encoding an enzyme having AIR synthetase activity has been cloned and its sequence has been determined (Senecoff and Meagher (1993) Plant Physiol. 102: 387–399; Schnorr et al. (1994) The Plant Journal, 6: 113–121).

II. Herbicide Discovery

The use of herbicides to control undesirable vegetation such as weeds in crop fields has become almost a universal practice. The herbicide market exceeds 15 billion dollars annually. Despite this extensive use, weed control remains a significant and costly problem for farmers.

Effective use of herbicides requires sound management. For instance, the time and method of application and stage of weed plant development are critical to getting good weed control with herbicides. Since various weed species are resistant to herbicides, the production of effective new herbicides becomes increasingly important. Novel herbicides can now be discovered using high-throughput screens that implement recombinant DNA technology. Metabolic enzymes found to be essential to plant growth and development can be recombinantly produced though standard molecular biological techniques and utilized as herbicide targets in screens for novel inhibitors of the enzymes' activity. The novel inhibitors discovered through such screens may then be used as herbicides to control undesirable vegetation.

III. Herbicide Tolerant Plants

Herbicides that exhibit greater potency, broader weed spectrum, and more rapid degradation in soil can also, unfortunately, have greater crop phytotoxicity. One solution applied to this problem has been to develop crops that are resistant or tolerant to herbicides. Crop hybrids or varieties tolerant to the herbicides allow for the use of the herbicides to kill weeds without attendant risk of damage to the crop. Development of tolerance can allow application of a herbicide to a crop where its use was previously precluded or limited (e.g. to pre-emergence use) due to sensitivity of the crop to the herbicide. For example, U.S. Pat. No. 4,761,373 to Anderson et al. is directed to plants resistant to various imidazolinone or sulfonamide herbicides. The resistance is conferred by an altered acetohydroxyacid synthase (AHAS) enzyme. U.S. Pat. No. 4,975,374 to Goodman et al. relates to plant cells and plants containing a gene encoding a mutant glutamine synthetase (GS) resistant to inhibition by herbicides that were known to inhibit GS, e.g. phosphinothricin and methionine sulfoximine. U.S. Pat. No. 5,013,659 to Bedbrook et al. is directed to plants expressing a mutant acetolactate synthase that renders the plants resistant to inhibition by sulfonylurea herbicides. U.S. Pat. No. 5,162,602 to Somers et al. discloses plants tolerant to inhibition by cyclohexanedione and aryloxyphenoxypropanoic acid herbicides. The tolerance is conferred by an altered acetyl coenzyme A carboxylase (ACCase).

SUMMARY OF THE INVENTION

One object of the present invention is to provide methods for identifying new or improved herbicides. Another object of the invention is to provide methods for using such new or improved herbicides to suppress the growth of plants such as weeds. Still another object of the invention is to provide improved crop plants that are tolerant to such new or improved herbicides.

Using an antisense validation system which allows for the inactivation of expression of an endogenous gene, the inventors of the present invention have demonstrated that the 5'-phosphoribosyl-5-aminoimidazole (AIR) synthetase activity is essential in plants. This implies that chemicals which inhibit AIR synthetase in plants are likely to have detrimental effects on plants and are potentially good herbicide candidates. The present invention therefore provides methods of using a purified AIR synthetase to identify inhibitors thereof, which can then be used as herbicides to suppress the growth of undesirable vegetation, e.g. in fields where crops are grown, particularly agronomically important crops such as maize and other cereal crops such as wheat, oats, rye, sorghum, rice, barley, millet, turf and forage grasses, and the like, as well as cotton, sugar cane, sugar beet, oilseed rape, and soybeans.

The present invention discloses for the first time the correct nucleotide sequence of the Arabidopsis AIR synthetase gene. The nucleotide sequence encoding the pre-protein is set forth in SEQ ID NO:1 and the nucleotide sequence encoding the putative mature protein is set forth in SEQ ID NO:3. The correct amino acid sequence of the Arabidopsis AIR synthetase pre-protein is set forth in SEQ ID NO:2 and of the correct amino acid sequence of the putative mature Arabidopsis AIR synthetase is set forth in SEQ ID NO:4. The present invention also encompasses plant enzymes having AIR synthetase activity and whose amino acid sequence are substantially similar to the amino acid sequences set forth in SEQ ID NO:2 and SEQ ID NO:4.

In a preferred embodiment, the present invention describes a method for identifying a chemical to be tested for the ability to inhibit plant growth or viability, comprising the steps of: (a) combining an enzyme having AIR synthetase activity in a first reaction mixture with a substrate of AIR synthetase under conditions in which the enzyme is capable of catalyzing the synthesis of AIR; (b) combining the chemical to be tested and the enzyme in a second reaction mixture with a substrate of AIR synthetase under the same conditions and for the same period of time as in the first reaction mixture; (c) determining the activity of the enzyme in the first and second reaction mixtures; and (d) selecting the chemical to be tested for the ability to inhibit plant growth or viability when the activity of the enzyme in the second reaction mixture is less, desirably significantly less, than the activity of the enzyme in the first reaction mixture. In a preferred embodiment, the substrate of AIR synthetase is 5'-phosphoribosyl-N-formylglycinamidine (FGAM) and in a further preferred embodiment, the substrate of AIR synthetase is β-FGAM. In another preferred embodiment, the enzyme having AIR synthetase activity is derived from a plant and more preferably, is encoded by a nucleotide sequence identical or substantially similar to the nucleotide sequence set forth in SEQ ID NO:1 or SEQ ID NO:3. In another embodiment, the AIR synthetase enzyme is encoded by a nucleotide sequence capable of encoding the amino acid sequence of SEQ ID NO:2 or SEQ ID NO:4. In yet another embodiment, the AIR synthetase enzyme has an amino acid sequence identical or substantially similar to the amino acid sequence set forth in SEQ ID NO:2 or SEQ ID NO:4. In another preferred embodiment, the chemical is capable of inhibiting the growth or viability of a plant by inhibiting the activity of AIR synthetase in the plant. In yet another preferred embodiment, the activity of the enzyme is determined by measuring the AIR produced in the reaction mixture. In another preferred embodiment, the activity of the enzyme is determined by measuring the ADP derived from ATP in the reaction mixture.

In another preferred embodiment, the present invention describes a method for identifying chemicals A method for identifying a chemical to be tested for the ability to inhibit plant growth or viability, comprising the steps of: (a) combining an enzyme having 5'-phosphoribosyl-N-formylglycinamidine (FGAM) synthetase activity and an enzyme having AIR synthetase activity in a first reaction mixture with a substrate of FGAM synthetase under conditions in which the enzymes are capable of catalyzing the coupled synthesis of AIR; (b) combining the chemical and the enzymes in a second reaction mixture with a substrate of FGAM synthetase under the same conditions and the same period of time as in the first reaction mixture; (c) determining the activity of the coupled enzymes in the first and second reaction mixtures; and (d) selecting the chemical to be tested for the ability to inhibit plant growth or viability when the activity of the enzyme having AIR synthetase activity in the second reaction mixture is less, desirably significantly less, than the activity of the enzyme having AIR synthetase activity in the first reaction mixture. In a preferred embodiment, the substrate of FGAM synthetase is 5'-phosphoribosyl-N-formylglycinamide (FGAR) and in a further preferred embodiment, the substrate of FGAM synthetase is β-FGAR. In another preferred embodiment, the enzyme having AIR synthetase activity is derived from a plant and more preferably, is encoded by a nucleotide sequence identical or substantially similar to the nucleotide sequence set forth in SEQ ID NO:1 or SEQ ID NO:3. In another embodiment, the AIR synthetase enzyme is encoded by a nucleotide sequence capable of encoding the amino acid sequence of SEQ ID NO:2 or SEQ ID NO:4. In yet another embodiment, the AIR synthetase enzyme has an amino acid sequence identical or substantially similar to the amino acid sequence set forth in SEQ ID NO:2 or SEQ ID NO:4. In another preferred embodiment, the chemical is capable of inhibiting the growth or viability of a plant by inhibiting the activity of AIR synthetase in the plant. In yet another preferred embodiment, the activity of the enzyme is determined by measuring the AIR produced in the reaction mixture. In another preferred embodiment, the activity of the enzyme is determined by measuring the ADP derived from ATP in the reaction mixture.

The present invention also further describes an assay comprising the steps of: (a) combining an enzyme having 5'-phosphoribosyl-N-formylglycinamidine (FGAM) synthetase activity and an enzyme having AIR synthetase activity in a first reaction mixture with a substrate of FGAM synthetase under conditions in which the enzymes are capable of catalyzing the coupled synthesis of AIR; (b) combining a chemical and the enzymes in a second reaction mixture with a substrate of FGAM synthetase under the same conditions and for the same period of time as in the first reaction mixture; (c) determining the activity of the enzyme having AIR synthetase activity in the first and second reaction mixtures; wherein the chemical is capable of inhibiting the activity of the enzyme having AIR synthetase activity if the activity of the enzyme having AIR synthetase activity in the second reaction mixture is less, desirably significantly less, than the activity of the enzyme having AIR synthetase activity in the first reaction mixture. In a preferred embodiment, the substrate of FGAM synthetase is 5'-phosphoribosyl-N-formylglycinamide (FGAR) and in a further preferred embodiment, the substrate of FGAM synthetase is β-FGAR. In yet another preferred embodiment, the activity of the enzyme is determined by measuring the AIR produced in the reaction mixture. In another preferred embodiment, the reaction mixture comprises ATP and the activity of the enzyme is determined by measuring the ADP derived from ATP in the reaction mixture.

In another preferred embodiment, the present invention describes a method for identifying chemicals having the ability to inhibit AIR synthetase in plants preferably comprising the steps of: a) obtaining transgenic plants, plant tissue, plant seeds or plant cells, preferably stably transformed, comprising a non-native nucleotide sequence encoding an enzyme having AIR synthetase activity and capable of overexpressing an enzymatically active AIR synthetase; b) applying the chemical to the transgenic plants, plant cells, tissues or parts and to the isogenic non-transformed plants, plant cells, tissues or parts; c) determining the growth or viability of the transgenic and non-transformed plants, plant cells, tissues after application of the chemical; d) comparing the growth or viability of the transgenic and non-transformed plants, plant cells, tissues after application of the chemical. Desirably, the chemical suppresses the viability or growth of the non-transgenic plants, plant cells, tissues or parts, without significantly suppressing the growth of the viability or growth of the isogenic transgenic plants, plant cells, tissues or parts. In a preferred embodiment, the enzyme having AIR synthetase activity is encoded by a nucleotide sequence identical or substantially similar to the nucleotide sequence set forth in SEQ ID NO:1 or SEQ ID NO:3. In another embodiment, the AIR synthetase enzyme is encoded by a nucleotide sequence capable of encoding the amino acid sequence of SEQ ID NO:2 or SEQ ID NO:4. In yet another embodiment, the AIR synthetase enzyme has an amino acid sequence identical or substantially similar to the amino acid sequence set forth in SEQ ID NO:2 or SEQ ID NO:4.

The present invention further embodies plants, plant tissues, plant seeds, and plant cells that have modified AIR synthetase activity and that are therefore tolerant to inhibition by a herbicide at levels normally inhibitory to naturally occurring AIR synthetase activity. Herbicide tolerant plants encompassed by the invention include those that would otherwise be potential targets for normally inhibiting herbicides, particularly the agronomically important crops mentioned above. According to this embodiment, plants, plant tissue, plant seeds, or plant cells are transformed, preferably stably transformed, with a recombinant DNA molecule comprising a suitable promoter functional in plants operatively linked to a nucleotide coding sequence that encodes a modified AIR synthetase that is tolerant to inhibition by a herbicide at a concentration that would normally inhibit the activity of wild-type, unmodified AIR synthetase. Modified AIR synthetase activity may also be conferred upon a plant by increasing expression of wild-type herbicide-sensitive AIR synthetase by providing multiple copies of wild-type AIR synthetase genes to the plant or by overexpression of wild-type AIR synthetase genes under control of a stronger-than-wild-type promoter. The transgenic plants, plant tissue, plant seeds, or plant cells thus created are then selected by conventional selection techniques, whereby herbicide tolerant lines are isolated, characterized, and developed. Alternately, random or site-specific mutagenesis may be used to generate herbicide tolerant lines.

Therefore, the present invention provides a plant, plant cell, plant seed, or plant tissue transformed with a DNA molecule comprising a nucleotide sequence isolated from a plant that encodes an enzyme having AIR synthetase activity, wherein the enzyme has AIR synthetase activity and wherein the DNA molecule confers upon the plant, plant cell, plant seed, or plant tissue tolerance to a herbicide in amounts that normally inhibits naturally occurring AIR synthetase activity. According to one example of this embodiment, the enzyme having AIR synthetase activity is encoded by a nucleotide sequence identical or substantially similar to the nucleotide sequence set forth in SEQ ID NO:1 or SEQ ID NO:3, or has an amino acid sequence identical or substantially similar to the amino acid sequence set forth in SEQ ID NO:2 or SEQ ID NO:4.

The invention also provides a method for suppressing the growth of a plant comprising the step of applying to the plant a chemical that inhibits the naturally occurring AIR synthetase activity in the plant. In a related aspect, the present invention is directed to a method for selectively suppressing the growth of weeds in a field containing a crop of planted crop seeds or plants, comprising the steps of: (a) planting herbicide tolerant crops or crop seeds, which are plants or plant seeds that are tolerant to a herbicide that inhibits the naturally occurring AIR synthetase activity; and (b) applying to the crops or crop seeds and the weeds in the field a herbicide in amounts that inhibit naturally occurring AIR synthetase activity, wherein the herbicide suppresses the growth of the weeds without significantly suppressing the growth of the crops.

Other objects and advantages of the present invention will become apparent to those skilled in the art from a study of the following description of the invention and non-limiting examples.

DEFINITIONS

For clarity, certain terms used in the specification are defined and presented as follows:

Activatable DNA Sequence: a DNA sequence that regulates the expression of genes in a genome, desirably the genome of a plant. The activatable DNA sequence is complementary to a target gene endogenous in the genome. When the activatable DNA sequence is introduced and expressed in a cell, it inhibits expression of the target gene. An activatable DNA sequence useful in conjunction with the present invention includes those encoding or acting as dominant inhibitors, such as a translatable or untranslatable sense sequence capable of disrupting gene function in stably transformed plants to positively identify one or more genes essential for normal growth and development of a plant. A preferred activatable DNA sequence is an antisense DNA sequence. The target gene preferably encodes a protein, such as a biosynthetic enzyme, receptor, signal transduction protein, structural gene product, or transport protein that is essential to the growth or survival of the plant. In an especially preferred embodiment, the target gene encodes an enzyme having AIR synthetase activity. The interaction of the antisense sequence and the target gene results in substantial inhibition of the expression of the target gene so as to kill the plant, or at least inhibit normal plant growth or development.

Activatable DNA Construct: a recombinant DNA construct comprising a synthetic promoter operatively linked to the activatable DNA sequence, which when introduced into a cell, desirably a plant cell, is not expressed, i.e. is silent, unless a complete hybrid transcription factor capable of binding to and activating the synthetic promoter is present. The activatable DNA construct is introduced into cells, tissues, or plants to form stable transgenic lines capable of expressing the activatable DNA sequence.

Co-factor: natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone.

Coupled synthesis: a enzymatic biosynthesis, in which a final product is synthesized by two sequential enzymatic steps, wherein the substrate for the first enzymatic step is converted by the first enzyme to an intermediate product, which serves as a substrate for the second enzymatic step and is converted by the second enzyme to the final product, without external addition of the intermediate product.

DNA shuffling: DNA shuffling is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA.

Enzyme activity: means herein the ability of an enzyme to catalyze the conversion of a substrate into a product. A substrate for the enzyme comprises the natural substrate of the enzyme but also comprises analogues of the natural substrate which can also be converted by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Herbicide: a chemical substance used to kill or suppress the growth of plants, plant cells, plant seeds, or plant tissues.

Heterologous DNA Sequence: a DNA sequence not naturally associated with a host cell into which it is introduced, including non-naturally occurring multiple copies of a naturally occurring DNA sequence.

Homologous DNA Sequence: a DNA sequence naturally associated with a host cell into which it is introduced.

Inhibitor: a chemical substance that inactivates the enzymatic activity of a protein such as a biosynthetic enzyme, receptor, signal transduction protein, structural gene product, or transport protein that is essential to the growth or survival of the plant. In the context of the instant invention, an inhibitor is a chemical substance that inactivates the enzymatic activity of AIR synthetase from a plant. The term "herbicide" is used herein to define an inhibitor when applied to plants, plant cells, plant seeds, or plant tissues.

Isogenic: plants which are genetically identical, except that they may differ by the presence or absence of a transgene.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, a transgenic host cell.

Mature protein: protein which is normally targeted to a cellular organelle, such as a chloroplast, and from which the transit peptide has been removed.

Minimal Promoter: promoter elements, particularly a TATA element, that are inactive or that have greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Pre-protein: protein which is normally targeted to a cellular organelle, such as a chloroplast, and still comprising its transit peptide.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is larger than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 65%, more desirably at least 75%, preferably at least 85%, more preferably at least 90%, still more preferably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or on the World Wide Web at hto.usc.edu/software/seqaln/index.html). The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mnM EDTA at 50° C. with washing in 0.1×SSC, 0.1% SDS at 65° C.

The term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 65%, more desirably at least 75%, preferably at least 85%, more preferably at least 90%, still more preferably at least 95%, yet still more preferably at least 99%.

Substrate: a substrate is the molecule that the enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Tolerance: the ability to continue normal growth or function when exposed to an inhibitor or herbicide.

Transformation: a process for introducing heterologous DNA into a cell, tissue, or plant. Transformed cells, tissues, or plants are understood to encompass not only the end product of a transformation process, but also transgenic progeny thereof.

Transgenic: stably transformed with a recombinant DNA molecule that preferably comprises a suitable promoter operatively linked to a DNA sequence of interest.

BRIEF DESCRIPTION OF THE SEQUENCES IN THE SEQUENCE LISTING

SEQ ID NO:1 DNA sequence encoding the Arabidopsis AIR synthetase pre-protein
SEQ ID NO:2 amino acid sequence of the Arabidopsis AIR synthetase pre-protein
SEQ ID NO:3 DNA sequence encoding the putative mature Arabidopsis AIR synthetase
SEQ ID NO:4 amino acid sequence of the putative mature Arabidopsis AIR synthetase
SEQ ID NO:5 oligonucleotide JG-L
SEQ ID NO:6 oligonucleotide AS-1
SEQ ID NO:7 oligonucleotide AS-2
SEQ ID NO:8 oligonucleotide slp242
SEQ ID NO:9 oligonucleotide slp244
SEQ ID NO:10 oligonucleotide slp243

DEPOSIT

The following material was deposited with the Agricultural Research Service, Patent Culture Collection (NRRL), 1815 North University Street, Peoria, Ill. 61604, under the terms of the Budapest Treaty on the International Recognition of the Deposit of Microorganisms for the Purposes of Patent Procedure. All restrictions on the availability of the deposited material will be irrevocably removed upon granting of the patent.

| Clone | Accession number | Date of Deposit |
| --- | --- | --- |
| DH5αpASM | NRRL B-21976 | April 17, 1998 |

DETAILED DESCRIPTION OF THE INVENTION

I. Correct Sequence of the Arabidopsis AIR Synthetase Gene

The Arabidopsis AIR synthetase gene was re-sequenced by the inventors of the present invention and compared to a published DNA sequence for the Arabidopsis AIR synthetase gene (Genbank accession L12457, Senecoff and Meagher (1993) Plant Physiol. 102: 387–399). Sequencing results revealed a substantial error in the published DNA sequence, resulting in the insertion of a cytosine base at the position corresponding to position 1,027 in SEQ ID NO:1. This insertion is leading to a frame-shift mutation in the amino acid sequence and therefore teaches away from the correct deduced amino acid sequence for the Arabidopsis AIR synthetase. The present invention discloses for the first time the correct nucleotide sequence of the Arabidopsis AIR synthetase gene as well as the correct amino acid sequence of the Arabidopsis AIR synthetase. The nucleotide sequence encoding the pre-protein is set forth in SEQ ID NO:1 and the nucleotide sequence encoding the mature protein is set forth in SEQ ID NO:3. The correct amino acid sequence of the Arabidopsis AIR synthetase pre-protein encoded by the nucleotide sequence set forth in SEQ ID NO:1 is set forth in SEQ ID NO:2 and the correct amino acid sequence of the putative mature Arabidopsis AIR synthetase encoded by the nucleotide sequence set forth in SEQ ID NO:2 is set forth in SEQ ID NO:4. The nucleotide sequence encoding the Arabidopsis AIR synthetase pre-protein was deposited in *E. coli* strain DH5αpASM and designated as NRRL accession number B-21976. The present invention also encompasses an isolated amino acid sequence derived from a plant, wherein said amino acid sequence is identical or substantially similar to the amino acid sequence encoded by the nucleotide sequence set forth in SEQ ID NO:1 or SEQ ID NO:3, wherein said amino acid sequence has 5'-phosphoribosyl-5-aminoimidazole (AIR) synthetase activity. The present invention also further encompasses an isolated amino acid sequence derived from a plant, wherein said amino acid sequence is identical or substantially similar to the amino acid sequence set forth in SEQ ID NO:2 or SEQ ID NO:4, wherein said amino acid sequence has 5'-phosphoribosyl-5-aminoimidazole (AIR) synthetase activity.

II. Essentiality of the AIR Synthetase Gene in Plants Demonstrated by Antisense Inhibition As shown in the examples below, the essentiality of the AIR synthetase gene for normal plant growth and development has been demonstrated for the first time by antisense inhibition in plants using the antisense validation system described in co-owned and co-pending application Ser. No. 08/978,830 [entitled "Methods and Compositions Useful for the Activation of Silent Transgenes", filed Nov. 26, 1997], incorporated herein by reference. Having established the essentiality of AIR synthetase function in plants, the inventors thereby provide an important and sought after tool for new herbicide development.

In the system described in the present invention, a hybrid transcription factor gene is made that comprises a DNA-binding domain and an activation domain. In addition, an activatable DNA construct is made that comprises a synthetic promoter operatively linked to an activatable DNA sequence. The hybrid transcription factor gene and synthetic promoter are selected or designed such that the DNA binding domain of the hybrid transcription factor is capable of binding specifically to the synthetic promoter, which then activates expression of the activatable DNA sequence. A first plant is transformed with the hybrid transcription factor gene, and a second plant is transformed with the activatable DNA construct. The first plant and second plants are crossed to produce a progeny plant containing both the sequence encoding the hybrid transcription factor and the synthetic promoter, wherein the activatable DNA sequence is expressed in the progeny plant. In the preferred embodiment, the activatable DNA sequence is an antisense sequence capable of inactivating expression of an endogenous gene such as the AIR synthetase gene. Hence, the progeny plant will be unable to normally express the endogenous gene.

This antisense validation system is especially useful for allowing expression of traits that might otherwise be unrecoverable as constitutively driven transgenes. For instance, foreign genes with potentially lethal effect or antisense genes or dominant-negative mutations designed to abolish function of essential genes, while of great interest in basic studies of plant biology, present inherent experimental problems. Decreased transformation frequencies are often cited as evidence of lethality associated with a particular constitutively driven transgene, but negative results of this type are laden with alternative trivial explanations. The present invention is an important advancement in the field of agriculture because it allows stable maintenance and propagation of a test transgene separate from its expression. This ability to separate transgene insertion from expression is especially useful for firm conclusions about essentiality of gene function to be drawn. A substantial benefit of the present invention is that plant genes essential for normal growth or development can thus be identified in this manner. The identification of such genes provide useful targets for screening compound libraries for identification of effective herbicides. Below, the antisense validation system is described in greater detail:

A. Hybrid Transcription Factor Gene

A hybrid transcription factor gene for use in the antisense validation system described herein comprises DNA sequences encoding (1) a DNA-binding domain and (2) an activation domain that interacts with components of transcriptional machinery assembling at a promoter. Gene fragments are joined, typically such that the DNA binding domain is toward the 5' terminus and the activator domain is toward the 3' terminus, to form a hybrid gene whose expression produces a hybrid transcription factor. One skilled in the art is capable of routinely combining various DNA sequences encoding DNA binding domains with various DNA sequences encoding activation domains to produce a wide array of hybrid transcription factor genes. Examples of DNA sequences encoding DNA binding domains include, but are not limited to, those encoding the DNA binding domains of GAL4, bacteriophage 434, lexA, lacI, and phage lambda repressor. Examples of DNA sequences encoding the activation domain include, but are not limited to, those encoding the acidic activation domains of herpes simplex VP16, maize C1, and P1. In addition, suitable activation domains can be isolated by fusing DNA pieces from an organism of choice to a suitable DNA binding domain and selecting directly for function (Estruch et al., (1994) *Nucleic Acids Res.* 22: 3983–3989). Domains of transcriptional activator proteins can be swapped between proteins of diverse origin (Brent and Ptashne (1985) *Cell* 43: 729–736). A preferable hybrid transcription factor gene comprises DNA sequences encoding the GAL4 DNA binding domain fused to the maize C1 activation domain.

B. Activatable DNA Construct

An activatable DNA construct for use in the antisense validation system described herein comprises (1) a synthetic promoter operatively linked to (2) an activatable DNA sequence. The synthetic promoter comprises at least one DNA binding site recognized by the DNA binding domain of the hybrid transcription factor, and a minimal promoter, preferably a TATA element derived from a promoter recognized by plant cells. More particularly the TATA element is derived from a promoter recognized by the plant cell type into which the synthetic promoter will be incorporated. Desirably, the DNA binding site is repeated multiple times in the synthetic promoter so that the minimal promoter may be more effectively activated, such that the activatable DNA sequence associated with the synthetic promoter is more effectively expressed. One skilled in the art can use routine molecular biology and recombinant DNA technology to make desirable synthetic promoters. Examples of DNA binding sites that can be used to make synthetic promoters useful in the invention include, but are not limited to, the upstream activating sequence ($UAS_G$) recognized by the GAL4 DNA binding protein, the lac operator, and the lexA binding site. Examples of promoter TATA elements recognized by plant cells include those derived from CaMV 35S, the maize Bzl promoter, and the UBQ3 promoter. An especially preferable synthetic promoter comprises a truncated CaMV 35S sequence containing the TATA element (nucleotides −59 to +48 relative to the start of transcription), fused at its 5' end to approximately 10 concatemeric direct repeats of the upstream activating sequence ($UAS_G$) recognized by the GAL4 DNA binding domain.

The activatable DNA sequence encompasses any DNA sequence for which stable introduction and expression in a plant cell is desired. Particularly desirable activatable DNA sequences are sense or antisense sequences, whose expression results in decreased expression of their endogenous counterpart genes, thereby inhibiting normal plant growth or development. The activatable DNA sequence is operatively linked to the synthetic promoter to form the activatable DNA construct. The activatable DNA sequence in the activatable DNA construct is not expressed, i.e. is silent, in transgenic lines, unless a hybrid transcription factor capable of binding to and activating the synthetic promoter, is also present. The activatable DNA construct subsequently is introduced into cells, tissues or plants to form stable transgenic lines expressing the activatable DNA sequence, as described more fully below. In the context of the present invention, the activatable DNA sequence preferably comprises an antisense AIR synthetase sequence.

C. Transgenic Plants Containing the Hybrid Transcription Factor Gene or the Activatable DNA Construct The antisense validation system described herein utilizes a first plant containing the hybrid transcription factor gene and a second plant containing the activatable DNA construct. The hybrid transcription factor genes and activatable DNA constructs described above are introduced into the plants by methods well known and routinely used in the art, including but not limited to crossing, Agrobacterium-mediated transformation, Ti plasmid vectors, direct DNA uptake such as microprojectile bombardment, liposome mediated uptake, micro-injection, etc. Transformants are screened for the presence and functionality of the transgenes according to standard methods known to those skilled in the art.

D. Transgenic Plants Containing Both the Hybrid Transcription Factor Gene and the Activatable DNA Construct F1 plants containing both the hybrid transcription factor gene and the activatable DNA construct are generated by cross-pollination and selected for the presence of an appropriate marker. In contrast to plants containing the activatable DNA construct alone, the F1 plants generate high levels of activatable DNA sequence expression product, comparable to those obtained with strong constitutive promoters such as CaMV 35S.

E. Antisense Validation Assay

Thus, a useful assay in the system described herein comprises the following steps: a) providing a first transgenic plant stably transformed with a hybrid transcription factor gene encoding a hybrid transcription factor capable of activating a synthetic promoter when said synthetic promoter is present in the plant, wherein the first transgenic plant is homozygous for the hybrid transcription factor; b) providing a second transgenic plant stably transformed with an activatable DNA construct comprising a synthetic promoter activatable by the hybrid transcription factor of step a) operatively linked to an activatable DNA sequence, such as an antisense AIR synthetase sequence; c) crossing the first transgenic plant with the second transgenic plant to yield F1 plants expressing the activatable DNA sequence, in the presence of the hybrid transcription factor; and d) determining the effect of expression of the activatable DNA sequence on the F1 plants.

III. Recombinant Production of AIR Synthetases and Uses Thereof

For recombinant production of AIR synthetase in a host organism, a nucleotide sequence encoding an enzyme having AIR synthetase is inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli*, yeast, and insect cells (see, e.g., Luckow and Summers, *Bio/Technol.* 6: 47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica california* nuclear polyhedrosis virus (AcMNPV). A preferred baculovirus/insect system is pV111392/Sf21 cells (Invitrogen, La Jolla, Calif.).

In a preferred embodiment, the nucleotide sequence encoding an enzyme having a AIR synthetase activity is derived from an eukaryote, such as a mammal, a fly or a yeast, but is preferably derived from a plant. In a further preferred embodiment, the nucleotide sequence is identical or substantially similar to the nucleotide sequence set forth in SEQ ID NO:1 or SEQ ID NO:3, or encodes an enzyme having AIR synthetase activity, whose amino acid sequence is identical or substantially similar to the amino acid sequence set forth in SEQ ID NO:2 or SEQ ID NO:4. The nucleotide sequence set forth in SEQ ID NO:1 encodes the Arabidopsis AIR synthetase pre-protein, whose amino acid sequence is set forth in SEQ ID NO:2, and the nucleotide sequence set forth in SEQ ID NO:3 encodes the Arabidopsis putative mature AIR synthetase, whose amino acid sequence is set forth in SEQ ID NO:4. In another preferred embodiment, the nucleotide sequence is derived from a prokaryote, preferably a bacteria, e.g. *E. coli*. In this case, the enzyme having AIR synthetase activity is encoded by the purM gene.

Recombinantly produced AIR synthetases are isolated and purified using a variety of standard techniques. The actual techniques that may be used will vary depending upon the host organism used, whether the enzyme is designed for secretion, and other such factors familiar to the skilled artisan (see, e.g. chapter 16 of Ausubel, F. et al., "Current Protocols in Molecular Biology", pub. by John Wiley & Sons, Inc. (1994).

Recombinantly produced AIR synthetases are useful for a variety of purposes. For example, they can be used in in vitro assays to screen known herbicidal chemicals whose target has not been identified to determine if they inhibit AIR synthetases. Such in vitro assays may also be used as more general screens to identify chemicals that inhibit such enzymatic activity and that are therefore novel herbicide candidates. Alternatively, recombinantly produced AIR synthetases may be used to elucidate the complex structure of these molecules and to further characterize their association with known inhibitors in order to rationally design new inhibitory herbicides as well as herbicide tolerant forms of the enzymes.

IV. In Vitro Inhibitor Assay

An in vitro assay useful for identifying inhibitors of enzymes encoded by essential plant genes, such as the AIR synthetase, preferably comprises the steps of: a) reacting an enzyme having AIR synthetase activity and a substrate thereof in the presence of a suspected inhibitor of the enzyme's function; b) comparing the rate of enzymatic activity in the presence of the suspected inhibitor to the rate of enzymatic activity under the same conditions in the absence of the suspected inhibitor; and c) determining whether the suspected inhibitor inhibits the AIR synthetase enzymatic activity. In a preferred embodiment, such a determination is made by comparing, in the presence and absence of the candidate inhibitor, the amount of AIR synthesized in the in vitro assay using fluorescence or absorbance detection. In another preferred embodiment, such a determination is made by comparing, in the presence and absence of the candidate inhibitor, the amount of ADP formed in the in vitro assay using fluorescence or absorbance detection. A preferred substrate for AIR synthetase is 5'-phosphoribosyl-N-formylglycinamidine (FGAM), in particular the β isomer, β-FGAM.

In another preferred embodiment, a coupled FGAM synthetase/AIR synthetase assay is used, thereby increasing the detection limit of the assay and resulting in an improved screening procedure for a chemical inhibiting AIR synthetase activity. Such a coupling assay preferably comprises the steps of: a) reacting an enzyme having 5'-phosphoribosyl-N-formylglycinamidine (FGAM) synthetase activity, an enzyme having AIR synthetase activity and a substrate of FGAM synthetase in the presence of a suspected inhibitor of the enzyme's function; b) comparing the rate of enzymatic activity in the presence of the suspected inhibitor to the rate of enzymatic activity under the same conditions in the absence of the suspected inhibitor; and c) determining whether the suspected inhibitor inhibits the AIR synthetase enzymatic activity. In a preferred embodiment, such a determination is made by comparing, in the presence and absence of the candidate inhibitor, the amount of AIR synthesized in the in vitro assay using fluorescence or absorbance detection. In another preferred embodiment, such a determination is made by comparing, in the presence and absence of the candidate inhibitor, the amount of ADP formed in the in vitro assay using fluorescence or absorbance detection. A preferred substrate for FGAM synthetase is 5'-phosphoribosyl-N-formylglycinamide (FGAR), in particular the β isomer, β-FGAR. In a further preferred embodiment, the enzyme having FGAM synthetase activity is derived from a bacteria, and is preferably the *E. coli* FGAM synthetase encoded by the purL gene. The purL gene is preferably recombinantly produced in *E. coli*. While any suitable AIR synthetase may be used, preferably the AIR synthetase used in such in vitro assays is derived from a plant. In another preferred embodiment, an assay coupling more than one enzymatic activity preceding AIR synthetase in the purine biosynthesis pathway is used.

In a preferred embodiment, an enzyme used in an in vitro assay is derived from cells comprising the enzyme, preferably, from a crude extract of the cells. The enzyme is preferably isolated and purified from the cells or from the crude extract. The enzyme is preferably produced recombinantly and is preferably isolated and purified prior to be used in the assay. Chemicals identified in an in vitro assay are then tested for their ability to inhibit plant growth or viability.

V. In Vivo Inhibitor Assay

A. In one embodiment, a suspected herbicide, for example identified by in vitro screening, is applied to plants at various concentrations. The suspected herbicide is preferably sprayed on the plants. After application of the suspected herbicide, its effect on the plants, for example death or suppression of growth is recorded.

B. In another embodiment, an in vivo screening assay for inhibitors of the AIR synthetase activity uses transgenic plants, plant tissue, plant seeds or plant cells capable of overexpressing a nucleotide sequence having AIR synthetase activity, wherein the AIR synthetase is enzymatically active in the transgenic plants, plant tissue, plant seeds or plant cells. The nucleotide sequence is preferably derived from an eukaryote, such as a mammal, a fly or a yeast, but is preferably derived from a plant. In a further preferred embodiment, the nucleotide sequence is identical or substantially similar to the nucleotide sequence set forth in SEQ ID NO:1 or SEQ ID NO:3, or encodes an enzyme having AIR synthetase activity, whose amino acid sequence is identical or substantially similar to the amino acid sequence set forth in SEQ ID NO:2 or SEQ ID NO:4. In another preferred embodiment, the nucleotide sequence is derived from a prokaryote, preferably a bacteria, e.g. E. coli. In this case, the enzyme having AIR synthetase activity is encoded by the purM gene.

A chemical is then applied to the transgenic plants, plant tissue, plant seeds or plant cells and to the isogenic non-transformed plants, plant tissue, plant seeds or plant cells, and the growth or viability of the transgenic and non-transformed plants, plant tissue, plant seeds or plant cells are determined after application of the chemical and compared.

VI. Herbicide Tolerant Plants

The present invention is further directed to plants, plant tissue, plant seeds, and plant cells tolerant to herbicides that inhibit the naturally occurring AIR synthetase activity in these plants, wherein the tolerance is conferred by an altered AIR synthetase activity. Altered AIR synthetase activity may be conferred upon a plant according to the invention by increasing expression of wild-type herbicide-sensitive AIR synthetase by providing additional wild-type AIR synthetase genes to the plant, by expressing modified herbicide-tolerant AIR synthetases in the plant, or by a combination of these techniques. Representative plants include any plants to which these herbicides are applied for their normally intended purpose. Preferred are agronomically important crops such as cotton, soybean, oilseed rape, sugar beet, maize, rice, wheat, barley, oats, rye, sorghum, millet, turf, forage, turf grasses, and the like.

A. Increased Expression of Wild-Type AIR Synthetase

Achieving altered AIR synthetase activity through increased expression results in a level of a AIR synthetase in the plant cell at least sufficient to overcome growth inhibition caused by the herbicide. The level of expressed enzyme generally is at least two times, preferably at least five times, and more preferably at least ten times the natively expressed amount. Increased expression may be due to multiple copies of a wild-type AIR synthetase gene; multiple occurrences of the coding sequence within the gene (i.e. gene amplification) or a mutation in the non-coding, regulatory sequence of the endogenous gene in the plant cell. Plants having such altered gene activity can be obtained by direct selection in plants by methods known in the art (see, e.g. U.S. Pat. Nos. 5,162,602, and 4,761,373, and references cited therein). These plants also may be obtained by genetic engineering techniques known in the art. Increased expression of a herbicide-sensitive AIR synthetase gene can also be accomplished by transforming a plant cell with a recombinant or chimeric DNA molecule comprising a promoter capable of driving expression of an associated structural gene in a plant cell operatively linked to a homologous or heterologous structural gene encoding the AIR synthetase. Preferably, the transformation is stable, thereby providing a heritable transgenic trait.

B. Expression of Modified Herbicide-Tolerant AIR Synthetases

According to this embodiment, plants, plant tissue, plant seeds, or plant cells are stably transformed with a recombinant DNA molecule comprising a suitable promoter functional in plants operatively linked to a coding sequence encoding a herbicide tolerant form of an AIR synthetase. A herbicide tolerant form of the enzyme has at least one amino acid substitution, addition or deletion that confers tolerance to a herbicide that inhibits the unmodified, naturally occurring form of the enzyme. The transgenic plants, plant tissue, plant seeds, or plant cells thus created are then selected by conventional selection techniques, whereby herbicide tolerant lines are isolated, characterized, and developed. Below are described methods for obtaining genes that encode herbicide tolerant forms of AIR synthetases:

One general strategy involves direct or indirect mutagenesis procedures on microbes. For instance, a genetically manipulatable microbe such as E. coli or S. cerevisiae may be subjected to random mutagenesis in vivo with mutagens such as UV light or ethyl or methyl methane sulfonate. Mutagenesis procedures are described, for example, in Miller, *Experiments in Molecular Genetics*, Cold Spring Harbor Laboratory, Cold Spring Harbor, N.Y. (1972); Davis et al., *Advanced Bacterial Genetics*, Cold Spring Harbor Laboratory, Cold Spring Harbor, N.Y. (1980); Sherman et al., *Methods in Yeast Genetics*, Cold Spring Harbor Laboratory, Cold Spring Harbor, N.Y. (1983); and U.S. Pat. No. 4,975,374. The microbe selected for mutagenesis contains a normal, inhibitor-sensitive AIR synthetase gene and is dependent upon the activity conferred by this gene. The mutagenized cells are grown in the presence of the inhibitor at concentrations that inhibit the unmodified gene. Colonies of the mutagenized microbe that grow better than the unmutagenized microbe in the presence of the inhibitor (i.e. exhibit resistance to the inhibitor) are selected for further analysis. AIR synthetase genes from these colonies are isolated, either by cloning or by PCR amplification, and their sequences are elucidated. Sequences encoding altered gene products are then cloned back into the microbe to confirm their ability to confer inhibitor tolerance.

A method of obtaining mutant herbicide-tolerant alleles of a plant AIR synthetase gene involves direct selection in plants. For example, the effect of a mutagenized AIR synthetase gene on the growth inhibition of plants such as Arabidopsis, soybean, or maize is determined by plating seeds sterilized by art-recognized methods on plates on a simple minimal salts medium containing increasing concentrations of the inhibitor. Such concentrations are in the range of 0.001, 0.003, 0.01, 0.03, 0.1, 0.3, 1, 3, 10, 30, 110, 300, 1000 and 3000 parts per million (ppm). The lowest dose at which significant growth inhibition can be reproducibly detected is used for subsequent experiments. Determination of the lowest dose is routine in the art.

Mutagenesis of plant material is utilized to increase the frequency at which resistant alleles occur in the selected population. Mutagenized seed material is derived from a variety of sources, including chemical or physical mutagenesis or seeds, or chemical or physical mutagenesis or pollen (Neuffer, In *Maize for Biological Research* Sheridan, ed. Univ. Press, Grand Forks, N. Dak., pp. 61–64 (1982)), which is then used to fertilize plants and the resulting $M_1$ mutant seeds collected. Typically for Arabidopsis, $M_2$ seeds (Lehle Seeds, Tucson, Ariz.), which are progeny seeds of plants grown from seeds mutagenized with chemicals, such as ethyl methane sulfonate, or with physical agents, such as gamma rays or fast neutrons, are plated at densities of up to 10,000 seeds/plate (10 cm diameter) on minimal salts medium containing an appropriate concentration of inhibitor to select for tolerance. Seedlings that continue to grow and remain green 7–21 days after plating are transplanted to soil and grown to maturity and seed set. Progeny of these seeds are tested for tolerance to the herbicide. If the tolerance trait is dominant, plants whose seed segregate 3:1/resistant:sensitive are presumed to have been heterozygous for the resistance at the $M_2$ generation. Plants that give rise to all resistant seed are presumed to have been homozygous for the resistance at the $M_2$ generation. Such mutagenesis on intact seeds and screening of their $M_2$ progeny seed can also be carried out on other species, for instance soybean (see, e.g. U.S. Pat. No. 5,084,082). Alternatively, mutant seeds to be screened for herbicide tolerance are obtained as a result of fertilization with pollen mutagenized by chemical or physical means.

Confirmation that the genetic basis of the herbicide tolerance is a modified AIR synthetase gene is ascertained as exemplified below. First, alleles of the AIR synthetase gene from plants exhibiting resistance to the inhibitor are isolated using PCR with primers based either upon the Arabidopsis cDNA coding sequences shown in SEQ ID NO:1 or, more preferably, based upon the unaltered AIR synthetase gene sequence from the plant used to generate tolerant alleles. After sequencing the alleles to determine the presence of mutations in the coding sequence, the alleles are tested for their ability to confer tolerance to the inhibitor on plants into which the putative tolerance-conferring alleles have been transformed. These plants can be either Arabidopsis plants or any other plant whose growth is susceptible to the AIR synthetase inhibitors. Second, the inserted AIR synthetase genes are mapped relative to known restriction fragment length polymorphisms (RFLPs) (See, for example, Chang et al. *Proc. Natl. Acad, Sci, USA* 85: 6856–6860 (1988); Nam et al., *Plant Cell* 1: 699–705 (1989). The AIR synthetase inhibitor tolerance trait is independently mapped using the same markers. When tolerance is due to a mutation in that AIR synthetase gene, the tolerance trait maps to a position indistinguishable from the position of the AIR synthetase gene.

Another method of obtaining herbicide-tolerant alleles of a AIR synthetase gene is by selection in plant cell cultures. Explants of plant tissue, e.g. embryos, leaf disks, etc. or actively growing callus or suspension cultures of a plant of interest are grown on medium in the presence of increasing concentrations of the inhibitory herbicide or an analogous inhibitor suitable for use in a laboratory environment. Varying degrees of growth are recorded in different cultures. In certain cultures, fast-growing variant colonies arise that continue to grow even in the presence of normally inhibitory concentrations of inhibitor. The frequency with which such faster-growing variants occur can be increased by treatment with a chemical or physical mutagen before exposing the tissues or cells to the inhibitor. Putative tolerance-conferring alleles of the AIR synthetase gene are isolated and tested as described in the foregoing paragraphs. Those alleles identified as conferring herbicide tolerance may then be engineered for optimal expression and transformed into the plant. Alternatively, plants can be regenerated from the tissue or cell cultures containing these alleles.

Still another method involves mutagenesis of wild-type, herbicide sensitive plant AIR synthetase genes in bacteria or yeast, followed by culturing the microbe on medium that contains inhibitory concentrations of the inhibitor and then selecting those colonies that grow in the presence of the inhibitor. More specifically, a plant cDNA, such as the Arabidopsis cDNA encoding the AIR synthetase is cloned into a microbe that otherwise lacks the selected gene's activity. The transformed microbe is then subjected to in vivo mutagenesis or to in vitro mutagenesis by any of several chemical or enzymatic methods known in the art, e.g. sodium bisulfite (Shortle et al., *Methods Enzymol.* 100:457–468 (1983); methoxylamine (Kadonaga et al., *Nucleic Acids Res.* 13:1733–1745 (1985); oligonucleotide-directed saturation mutagenesis (Hutchinson et al., *Proc. Natl. Acad. Sci. USA,* 83:710–714 (1986); or various polymerase misincorporation strategies (see, e.g. Shortle et al., *Proc. Natl. Acad. Sci. USA,* 79:1588–1592 (1982); Shiraishi et al., *Gene* 64:313–319 (1988); and Leung et al., *Technique* 1:11–15 (1989). Colonies that grow in the presence of normally inhibitory concentrations of inhibitor are picked and purified by repeated restreaking. Their plasmids are purified and tested for the ability to confer tolerance to the inhibitor by retransforming them into the microbe lacking AIR synthetase gene activity. The DNA sequences of cDNA inserts from plasmids that pass this test are then determined.

Herbicide resistant AIR synthetase enzymes are also obtained using methods involving in vitro recombination, also called DNA shuffling. By DNA shuffling, mutations, preferably random mutations, are introduced in AIR synthetase genes. DNA shuffling also leads to the recombination and rearrangement of sequences within an AIR synthetase genes or to recombination and exchange of sequences between two or more different of AIR synthetase genes. These methods allows for the production of millions of mutated AIR synthetase genes. The mutated genes, or shuffled genes, are screened for desirable properties, e.g. improved tolerance to herbicides and for mutations that provide broad spectrum tolerance to the different classes of inhibitor chemistry. Such screens are well within the skills of a routineer in the art.

In a preferred embodiment, a mutagenized AIR synthetase gene is formed from at least one template AIR synthetase gene, wherein the template AIR synthetase gene has been cleaved into double-stranded random fragments of a desired size, and comprising the steps of adding to the resultant population of double-stranded random fragments one or more single or double-stranded oligonucleotides, wherein said oligonucleotides comprise an area of identity and an area of heterology to the double-stranded random fragments; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide, wherein the mutagenized polynucleotide is a mutated AIR synthetase gene having enhanced tolerance to a herbicide which inhibits naturally occurring AIR synthetase activity. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles. Such method is described e.g. in Stemmer et al. (1994) Nature 370: 389–391, in U.S. Pat. No. 5,605,793 and in Crameri et al. (1998) Nature 391: 288–291, as well as in WO 97/20078, and these references are incorporated herein by reference.

In another preferred embodiment, any combination of two or more different AIR synthetase genes are mutagenized in vitro by a staggered extension process (StEP), as described e.g. in Zhao et al. (1998) Nature Biotechnology 16: 258–261. The two or more AIR synthetase genes are used as template for PCR amplification with the extension cycles of the PCR reaction preferably carried out at a lower temperature than the optimal polymerization temperature of the polymerase. For example, when a thermostable polymerase with an optimal temperature of approximately 72° C. is used, the temperature for the extension reaction is desirably below 72° C., more desirably below 65° C., preferably below 60° C., more preferably the temperature for the extension reaction is 55° C. Additionally, the duration of the extension reaction of the PCR cycles is desirably shorter than usually carried out in the art, more desirably it is less than 30 seconds, preferably it is less than 15 seconds, more preferably the duration of the extension reaction is 5 seconds. Only a short DNA fragment is polymerized in each extension reaction, allowing template switch of the extension products between the starting DNA molecules after each cycle of denaturation and annealing, thereby generating diversity among the extension products. The optimal number of cycles in the PCR reaction depends on the length of the AIR synthetase coding regions to be mutagenized but desirably over 40 cycles, more desirably over 60 cycles, preferably over 80 cycles are used. Optimal extension conditions and the optimal number of PCR cycles for every combination of AIR synthetase genes are determined as described in using procedures well-known in the art. The other parameters for the PCR reaction are essentially the same as commonly used in the art. The primers for the amplification reaction are preferably designed to anneal to DNA sequences located outside of the coding sequence of the AIR synthetase genes, e.g. to DNA sequences of a vector comprising the AIR synthetase genes, whereby the different AIR synthetase genes used in the PCR reaction are preferably comprised in separate vectors. The primers desirably anneal to sequences located less than 500 bp away from the AIR synthetase coding sequences, preferably less than 200 bp away from the AIR synthetase coding sequences, more preferably less than 120 bp away from the AIR synthetase coding sequences. Preferably, the AIR synthetase coding sequences are surrounded by restriction sites, which are included in the DNA sequence amplified during the PCR reaction, thereby facilitating the cloning of the amplified products into a suitable vector.

In another preferred embodiment, fragments of AIR synthetase genes having cohesive ends are produced as described in WO 98/05765. The cohesive ends are produced by ligating a first oligonucleotide corresponding to a part of a AIR synthetase gene to a second oligonucleotide not present in the gene or corresponding to a part of the gene not adjoining to the part of the gene corresponding to the first oligonucleotide, wherein the second oligonucleotide contains at least one ribonucleotide. A double-stranded DNA is produced using the first oligonucleotide as template and the second oligonucleotide as primer. The ribonucleotide is cleaved and removed. The nucleotide(s) located 5' to the ribonucleotide is also removed, resulting in double-stranded fragments having cohesive ends. Such fragments are randomly reassembled by ligation to obtain novel combinations of gene sequences.

Any AIR synthetase gene or any combination of AIR synthetase genes is used for in vitro recombination in the context of the present invention, for example, an AIR synthetase gene derived from a plant, such as, e.g. *Arabidopsis thaliana*, e.g. an AIR synthetase gene set forth in SEQ ID NO:1 or SEQ ID NO:3, an AIR synthetase gene from a bacteria, such as *Bacillus subtilis* (Ebbole and Zalkin (1987) J. Biol. Chem. 262: 8274–8287) or *E. coli* (Smith and Daum (1986) J. Biol. Chem. 261: 10632–10637), a human AIR synthetase gene (Aimi et al. (1990) Nucleic Acids Res. 18: 6665–6672), or an AIR synthetase gene from Drosophila (Henikoff et al. (1986) PNAS 289: 33–37), from chicken (Chen et al. (1990) PNAS 87: 3097–3101), and all incorporated herein by reference. Whole AIR synthetase genes or portions thereof are used in the context of the present invention. The library of mutated AIR synthetase genes obtained by the methods described above are cloned into appropriate expression vectors and the resulting vectors are transformed into an appropriate host, for example an algae like Chlamydomonas, a yeast or a bacteria. An appropriate host is preferably a host that otherwise lacks AIR synthetase gene activity, for example *E. coli* strain SØ6609/λKC (Schnorr et al. (1994) Plant Journal 6: 113–121). Host cells transformed with the vectors comprising the library of mutated AIR synthetase genes are cultured on medium that contains inhibitory concentrations of the inhibitor and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

An assay for identifying a modified AIR synthetase gene that is tolerant to an inhibitor may be performed in the same manner as the assay to identify inhibitors of the AIR synthetase activity (Inhibitor Assay, above) with the following modifications: First, a mutant AIR synthetase is substituted in one of the reaction mixtures for the wild-type AIR synthetase of the inhibitor assay. Second, an inhibitor of wild-type enzyme is present in both reaction mixtures. Third, mutated activity (activity in the presence of inhibitor and mutated enzyme) and unmutated activity (activity in the presence of inhibitor and wild-type enzyme) are compared to determine whether a significant increase in enzymatic activity is observed in the mutated activity when compared to the unmutated activity. Mutated activity is any measure of activity of the mutated enzyme while in the presence of a suitable substrate and the inhibitor. Unmutated activity is any measure of activity of the wild-type enzyme while in the presence of a suitable substrate and the inhibitor. A significant increase is defined as an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, most preferably an increase by about 10-fold or greater.

In addition to being used to create herbicide-tolerant plants, genes encoding herbicide tolerant AIR synthetases can also be used as selectable markers in plant cell transformation methods. For example, plants, plant tissue, plant seeds, or plant cells transformed with a transgene can also be transformed with a gene encoding an altered AIR synthetase capable of being expressed by the plant. The transformed cells are transferred to medium containing an inhibitor of the enzyme in an amount sufficient to inhibit the survivability of plant cells not expressing the modified gene, wherein only the transformed cells will survive. The method is applicable to any plant cell capable of being transformed with a modified AIR synthetase-encoding gene, and can be used with any transgene of interest. Expression of the transgene and the modified gene can be driven by the same promoter functional in plant cells, or by separate promoters.

VII. Plant Transformation Technology

A wild-type or herbicide-tolerant form of the AIR synthetase gene can be incorporated in plant or bacterial cells using conventional recombinant DNA technology. Generally, this involves inserting a DNA molecule encoding the AIR synthetase into an expression system to which the DNA molecule is heterologous (i.e., not normally present) using standard cloning procedures known in the art. The vector contains the necessary elements for the transcription and translation of the inserted protein-coding sequences in a host cell containing the vector. A large number of vector systems known in the art can be used, such as plasmids, bacteriophage viruses and other modified viruses. The components of the expression system may also be modified to increase expression. For example, truncated sequences, nucleotide substitutions or other modifications may be employed. Expression systems known in the art can be used to transform virtually any crop plant cell under suitable conditions. A transgene comprising a wild-type or herbicide-tolerant form of the AIR synthetase gene is preferably stably transformed and integrated into the genome of the host cells. In another preferred embodiment, the transgene comprising a wild-type or herbicide-tolerant form of the AIR synthetase gene located on a self-replicating vector. Examples of self-replicating vectors are viruses, in particular gemini viruses. Transformed cells can be regenerated into whole plants such that the chosen form of the AIR synthetase gene confers herbicide tolerance in the transgenic plants.

A. Requirements for Construction of Plant Expression Cassettes

Gene sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described infra. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters known in the art can be used. For example, for constitutive expression, the CaMV 35S promoter, the rice actin promoter, or the ubiquitin promoter may be used. For regulatable expression, the chemically inducible PR-1 promoter from tobacco or Arabidopsis may be used (see, e.g., U.S. Pat. No. 5,689,044).

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledonous and dicotyledonous plants.

3. Sequences for the Enhancement or Regulation of Expression

Numerous sequences have been found to enhance gene expression from within the transcriptional unit and these sequences can be used in conjunction with the genes of this invention to increase their expression in transgenic plants. For example, various intron sequences such as introns of the maize AdhI gene have been shown to enhance expression, particularly in monocotyledonous cells. In addition, a number of non-translated leader sequences derived from viruses are also known to enhance expression, and these are particularly effective in dicotyledonous cells.

4. Coding Sequence Optimization

The coding sequence of the selected gene may be genetically engineered by altering the coding sequence for optimal expression in the crop species of interest. Methods for modifying coding sequences to achieve optimal expression in a particular crop species are well known (see, e.g. Perlak et al., *Proc. Natl. Acad. Sci. USA* 88: 3324 (1991); and Koziel et al., *Bio/technol* 11: 194 (1993)).

5. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)). By the fusion of the appropriate targeting sequences described above to transgene sequences of interest it is possible to direct the transgene product to any organelle or cell compartment.

B. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Typical vectors suitable for Agrobacterium transformation include the binary vectors pCIB200 and pCIB2001, as well as the binary vector pCIB10 and hygromycin selection derivatives thereof. (See, for example, U.S. Pat. No. 5,639,949).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Typical vectors suitable for non-Agrobacterium transformation include pCIB3064, pSOG19, and pSOG35. (See, for example, U.S. Pat. No. 5,639,949).

C. Transformation Techniques

Once the coding sequence of interest has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells.

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. In each case the transformed cells are regenerated to whole plants using standard techniques known in the art.

Transformation of most monocotyledon species has now also become routine. Preferred techniques include direct gene transfer into protoplasts using PEG or electroporation techniques, particle bombardment into callus tissue, as well as Agrobacterium-mediated transformation.

VIII. Breeding

The wild-type or altered form of a AIR synthetase gene of the present invention can be utilized to confer herbicide tolerance to a wide variety of plant cells, including those of gymnosperms, monocots, and dicots. Although the gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The high-level expression of a wild-type AIR synthetase gene and/or the expression of herbicide-tolerant forms of a AIR synthetase gene conferring herbicide tolerance in plants, in combination with other characteristics important for production and quality, can be incorporated into plant lines through breeding approaches and techniques known in the art.

Where a herbicide tolerant AIR synthetase gene allele is obtained by direct selection in a crop plant or plant cell culture from which a crop plant can be regenerated, it is moved into commercial varieties using traditional breeding techniques to develop a herbicide tolerant crop without the need for genetically engineering the allele and transforming it into the plant.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Construction of a Vector Containing a GAL4 Binding Site/Minimal 35S CaMV Promoter Fused to Antisense AIR Synthetase pAT71

10 GAL4 binding sites and the minimal 35S promoter (−59 to +1) are excised from pGALLuc2 (Goff, et al., (1991) *Genes & Development* 5: 298–309) as an EcoRI-PstI fragment and inserted into the respective sites of pBluescript, yielding pAT52. pAT66 is constructed with a three-way ligation between the HindIII-PstI fragment of pAT52, a PstI-EcoRI fragment of pCIB1716 (contains a 35S untranslated leader, GUS gene, 35S terminator) and HindIII-EcoRI cut pUC18. The 35S leader of pAT66 is excised with PstI-NcoI and replaced with a PCR-generated 35S leader extending from +1 to +48 to yield pAT71.

pJG304

Plasmid pBS SK+ (Stratagene, LaJolla, Calif.) is linearized with SacI, treated with mung bean nuclease to remove the SacI site, and re-ligated with T4 ligase to make pJG201. The 10×GAL4 consensus binding site/CaMV 35S minimal promoter/GUS gene/CaMV terminator cassette is removed from pAT71 with KpnI and cloned into the KpnI site of pJG201 to make pJG304.

pJG304 is partially digested with restriction endonuclease Asp718 to isolate a full-length linear fragment. This fragment is ligated with a molar excess of the 22 base oligonucleotide JG-L (5' GTACCTCGAG TCTAGACTCG AG 3', SEQ ID NO:5). Restriction analysis is used to identify a clone with this linker inserted 5' to the GAL4 DNA binding site, and this plasmid is designated pJG304ΔXhoI.

pDG3

A fragment of the 5' phosphoribosyl-5-aminoimidazole (AIR) synthetase cDNA clone (Senecoff and Meagher (1993) Plant Physiology, 102: 387–399) is PCR-amplified from the *Arabidopsis thaliana* cDNA plasmid library pFL61 (Minet et al, (1992) Plant Journal, 2: 417–422) using the oligonucleotides AS-1 (5' GAT CGA GCT CGT TCT CTT CTG TGT CAT C 3', SEQ ID NO:6) and AS-2 (5' GAT CCC ATG GTC CCC AGG TAA AGA CGT C 3', SEQ ID NO:7).

The vector pJG304ΔXhoI is digested with SacI and NcoI to excise the GUS gene coding sequence. The AIR synthetase PCR fragment is digested with SacI and NcoI and ligated into pJG304ΔXhoI to make pDG3.

Example 2

Plant Transformation Vectors for AIR Synthetase Antisense Expression from the GAL4 Binding Site/CaMV Minimal 35S Promoter pJG261

Vector pGPTV (Becker, et al., (1992) *Plant Molecular Biology* 20: 1195–1197) is digested with EcoRI and HindIII to remove the nopaline synthase promoter/GUS cassette. Concurrently, the superlinker is excised from pSE380 (Invitrogen, San Diego, Calif.) with EcoRI and HindIII and cloned into the EcoRI/HindIII linearized pGPTV, to make pJG261.

PDG4 pDG3 is cut with XhoI to excise the cassette containing the GAL4 DNA binding site/35S minimal promoter/antisense AIR synthetase/CaMV terminator fusion. This cassette is ligated into XhoI digested pJG261, such that transcription is divergent from that of the BAR selectable marker, producing pDG4.

Example 3

Production of GAL4 Binding Site/Minimal CaMV 35S Antisense AIR Synthetase Transgenic Plants pDG4 is electro-transformed (Bio-Rad Laboratories, Hercules, Calif.) into *Agrobacterium tumefaciens* strain C58C1 (pMP90), and Arabidopsis plants (Ecotype Columbia) are transformed by infiltration (Bechtold et al, C. R. Acad. Sci. Paris, 316: 1188–93 (1993). Seeds from the infiltrated plants are selected on germination medium (Murashige-Skoog salts at 4.3 g/liter, Mes at 0.5 g/liter, 1% sucrose, thiamine at 10 ug/liter, pyridoxine at 5 ug/liter, nicotinic acid at 5 ug/liter, myo-inositol at 1 mg/liter, pH 5.8) containing Basta at 15 mg/liter.

Example 4

Production of GAL4/C1 Transactivator Transgenic Plants pSGZL1 is constructed by ligating the GAL4-C1 EcoRI fragment from pGALC1 (Goff, et al., (1991) *Genes & Development*, 5: 298–309) into the EcoRI site of pIC20H. The GAL4-C1 fragment of pSGZL1 is excised with BamHI-BglII and inserted into the BamHI site of pCIB770 (Rothstein, et al., (1987) *Gene* 53: 153–161) yielding pAT53.

Arabidopsis root explants are transformed with pAT53 as described in Valvekens, et al., (1985) PNAS USA 85: 5536–5540. Transgenic plants with single site insertion and positive for GAL4/C1 expression are taken to homozygosity.

Example 5

Antisense Inhibition of AIR Synthetase Using a GAL4/C1 Transactivator and a GAL4 Binding Site/Minimal CaMV 35S Promoter Fifteen transgenic plants containing the GAL4 binding site/minimal CaMV 35S promoter/antisense AIR synthetase construct are transplanted to soil and grown to maturity in the greenhouse. Flowers borne on the primary transformants are crossed to pollen from the homozygous GAL4/C1 transactivator line pAT53–103. F1 seeds are plated on germination medium and germination medium containing 15 mg/liter Basta. Seedlings from five F1 lines are transplanted to soil and grown to maturity in the greenhouse. Half of the seedlings from two F1 lines die while in soil. Half of the seedlings from three F1 lies are bleached and severely retarded in growth. These results show that the AIR synthetase gene is essential in plants.

Example 6

Expression of Recombinant Plant AIR Synthetase in *E. coli*

An *Arabidopsis thaliana* (Landsberg) cDNA library in the plasmid vector pFL61 (Minet et al., Plant J., 2:417–422 (1992)) is obtained and amplified. PCR primers to amplify protein coding sequence of Arabidopsis AIR synthetase are designed from a published DNA sequence (Genbank accession L12457, Senecoff and Meagher, Plant Physiol., 102: 387–399 (1993)) and used to amplify the AIR synthetase coding sequence from the plasmid library with Pfu DNA polymerase (Stratagene). Sequencing of the PCR product reveals an error in the published DNA sequence resulting in the insertion of a cytosine base at the position corresponding to position 1027 in SEQ ID NO:1, resulting in an incorrect predicted protein. Several other changes such as a 9 bp (=3 amino acid) insertion in the chloroplast transit peptide are observed but are probably due to variation between ecotypes. Primers are redesigned to correspond to the correct coding sequence. For the construct including the coding region of the AIR synthetase pre-protein, primers slp242 (5' CGC GGA TCC TCA CTA CTG ATA GCT TAC GCC TTC ACC 3', SEQ ID NO:8) and slp244 (5' TTG AAG CCA TGG AAG CTC GGA TTT TG 3', SEQ ID NO:9) are used, and for the construct including the coding region of the putative mature AIR synthetase, primers slp242 and slp243 (5' CGC ATG CCA TGG ATA AAG ATG ATG ACA CTG ATA GTC T 3', SEQ ID NO:10) are used. The coding-regions of the pre-protein and of the putative mature protein are subcloned into the expression vector pET32a (Novagen) and both are transformed into *E. coli* BL21 DE3 pLysS (Novagen) by electroporation using the Biorad Gene Pulser and the manufacturer's conditions.

Example 7

Growth and Extraction of FGAM Synthetase

*E. coli* strain TX635/pJS113 (Schendel et al. (1989) Biochemistry 28, 2459–2471) is grown in Luria broth (LB) containing 50 μg/mL carbenicillin at 30° C. in an incubator/shaker. When the cells reach an optical density of approximately 1 OD at 600 nm, an equal volume of LB carbenicillin at 56° C. is added to heat-shock the cells. Subsequently, the cells, are placed in an incubator-shaker and grown at 42° C. The cells are harvested at the end of log phase using low speed centrifugation. The centrifuge bottle is inverted and the media is allowed to drain. The cell pellet is resuspended with a small paintbrush in buffer A (50 mM EPPS, pH 7.5, 1 mM EDTA, 2 mM DTT, 150 mM KCl, 10% glycerol) and then disrupted in a french pressure cell at 18,000 PSI. Following a high speed centrifugation to remove cell debris, the enzyme is precipitated with ammonium sulfate (40–60%) and the pellets stored at −80° C. The enzyme is resuspended in a small volume of Buffer A and applied to a Sephadex G-25 column for desalting into Buffer A. The activity is assayed as described below.

Example 8

Growth and Extraction of AIR Synthetase

*E. coli* strain pJS24/Tx393 (Schrimsher et al. (1986) Biochemistry 25, 4366–4371) containing multiple gene copies of the native AIR synthetase is grown in LB broth containing 50 μg/mL of carbenicillin at 37° C. in an incubator-shaker. The cells are harvested at the end of the log phase of growth and pelleted in a centrifuge at low speed, the growth media is discarded and the centrifuge bottle is inverted and allowed to drain. The cells are resuspended in buffer A with a small paintbrush and disrupted in a French Pressure Cell at approximately 18,000 PSI. Following a high speed centrifugation to pellet cell debris, the supernatant is precipitated with ammonium sulfate and stored at −80° C.

Example 9
AIR synthetase Activity Assay

The AIR synthetase activity assay is essentially derived from Schrimsher et al. (1986) Biochemistry 25, 4356–4365. The reaction volumes are preferably the ones described below, but can be varied depending on the experimental requirements. $0.2-1.0\times10^{-4}$ unit of an enzyme having AIR synthetase activity (one unit of activity is defined as the amount of enzyme required to produce 1 μmol/min of product) and 0.1 mM 5'-phosphoribosyl-N-formylglycinamidine (FGAM) are mixed in a final volume of 96 μl 50 mM HEPES (pH 7.4–8.1, but preferably 7.7), 20 mM $MgCl_2$, 150 mM KCl and 0.01–10 mM, but preferably 2.0 mM ATP. The production of AIR is determined preferably according to Bratton and Marshall (J. Biol. Chem. (1939) 128, 537–550) by adding 32 μl of 1.33 M potassium phosphate in 20% (w/v) trichloroacetic acid (pH 1.4). The mixture is centrifuged to remove precipitated protein and 32 μl of 0.1% (w/v) sodium nitrite is added. After 3 min., 32 μl of 0.5% (w/v) ammonium sulfate is added and, after an additional minute, 8 μl of 25% N-(1-naphthyl) ethylenediamine dihydrochloride is added. The absorbance is measured at 530 nm after 10 min.

Alternatively, ADP formation is quantitated by a coupled reaction procedure. In this case, 3.5 units of pyruvate kinase, 4,7 units of lactate dehydrogenase, 1.0 mM phosphenolpyruvate and 0.2 mM NADH are added and absorbance is measured at 340 nm.

Example 10
Coupled FGAM Synthetase and AIR Synthetase Enzyme Assays
A. FGAM Synthetase Assay The conversion of FGAR to FGAM is followed by detecting the concommittant formation of ADP. The ADP formation is followed utilizing the enzymes pyruvate kinase, and lactate dehydrogenase (reagent enzymes) and detecting the conversion of NADH to $NAD^+$ in the presence of phosphoenolpyruvate (PEP). This is monitored at 340 nm. Pyruvate kinase and PEP facilitate the regeneration of ATP from ADP. ATP is a required substrate for both FGAM synthetase and AIR synthetase. The assay buffer is buffer A with the addition of 20 mM $MgCl_2$.
B. AIR Synthase Assay To assay AIR synthase it is necessary to provide the substrate FGAM. The FGAM is provided by the conversion of FGAR to FGAM in the same reaction mixture. If NADH is added the conversion can be followed utilizing the FGAM synthetase assay. When the FGAR-FGAM conversion proceeds sufficiently (approximately 50 μM) then AIR synthetase is added. Adding the AIR synthetase after the production of FGAM insures that the initial concentration of FGAM is constant in all reaction wells. The AIR synthetase is assayed by the method of Bratton and Marshall (J. Biol. Chem. (1939) 128, 537–550). After a sufficient time for AIR production (typically 15 minutes) the enzyme reaction is stopped with TCA. The AIR is derivatized with sodium nitrite and the nitrite is subsequently neutralized with ammonium sulfamate. The color is developed with the addition of N-(1-napthyl)ethylenediamine dihydrochloride (NEDD). After 10 minutes the color is monitored at 530 nm.
C. Assay Protocols The assays are carried out in the same way independent of the original source of the enzymes. The assays are performed in 300 μL 96 well microtiter plates. The total assay reaction volume is 200 μL. Substrates (except FGAR) are mixed in a ratio such that the final concentrations (in the microtiterplate) are as follows: L-glutamine (600 μM), ATP (600 μM), PEP (1 mM), and NADH (200 μM). A mixture of substrates at 10× concentration can be pipetted at 20 μL/well. The reagent enymes and FGAM synthetase can also be mixed to be added simultaneously. The suggested amounts of the ADP detecting/regeneration mix is 0.7 units pyruvate kinase and 0.97 units lactate dehydrogenase per reaction. This should be used as a guideline and the amounts of enzyme adjusted empirically. The FGAR (200 μM) should be added after a two minute incubation period. After the FGAM synthase reaction procedes to completion at a rate of approximately 10 μM/minute (this is within 10–15 minutes), the AIR synthetase is added. After an interval (determined by the activity of the AIR synthetase) the reaction is stopped with 66 μL of 20% TCA in 1M $K_3PO_4$. The plate in spun in a centrifuge to pellet the precipitated protein, then the supernatant is transferred to a separate microtiterplate for color development and reading. 1.2 μL of 10% sodium nitrite is added and after 3 minutes 1.2 μL of 50% ammonium sulfamate is added (neutralizes excess nitrite). One minute later, 8.3 μL of 1% NEDD are added and after 5 minutes, the plate is read at 530 nm using a microtiter plate reading UV/VIS spectrophotometer. AICAR is used as a standard since AIR is not available for that purpose. Based on AICAR a reasonable detection limit (3-fold OD over background) of 10 μM is easily attainable.

L-Glutamine, ATP, sodium nitrite, ammonium sulfamate, and NEDD, are available from Sigma Chemicals. FGAR is synthesized by the methods of Chen and Henderson (Can. J. Chemistry (1970) 48: 2306–2309) or Carrington et al. (J.Chem. Soc. (1968) 6864).

Example 11
In vitro Recombination of AIR Synthetase Genes by DNA Shuffling

The A. thaliana AIR synthetase gene encoding the preprotein is amplified by PCR as described in example 6. The resulting DNA fragment is digested by DNaseI treatment essentially as described (Stemmer et al. (1994) PNAS 91: 10747–10751) and the PCR primers are removed from the reaction mixture. A PCR reaction is carried out without primers and is followed by a PCR reaction with the primers, both as described (Stemmer et al. (1994) PNAS 91: 10747–10751). The resulting DNA fragments are cloned into pTRC99a (Pharmacia, Cat no: 27-5007-01) and transformed into E. coli strain SØ6609/λKC (Schnorr et al. (1994) Plant Journal 6: 113–121) by electroporation using the Biorad Gene Pulser and the manufacturer's conditions. The transformed bacteria are grown on medium that contains inhibitory concentrations of the inhibitor and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

In a similar reaction, PCR-amplified DNA fragments comprising the A. thaliana AIR synthetase gene encoding the pre-protein and PCR-amplified DNA fragments comprising the E. coli purM gene are recombined in vitro and resulting variants with improved tolerance to the inhibitor are recovered as described above.

Example 12
In vitro Recombination of AIR Synthetase Genes by Staggered Extension Process The A. thaliana AIR synthetase gene encoding the mature protein and the E. coli purM gene are each cloned into the polylinker of a pBluescript vector. A PCR reaction is carried out essentially as described (Zhao et al. (1998) Nature Biotechnology 16: 258–261) using the "reverse primer" and the "M13 20 primer" (Stratagene Catalog). Amplified PCR fragments are digested with appropriate restriction enzymes and cloned into pTRC99a and mutated AIR synthetase genes are screened as described in example 11.

The above disclosed embodiments are illustrative. This disclosure of the invention will place one skilled in the art in possession of many variations of the invention. All such obvious and foreseeable variations are intended to be encompassed by the appended claims.

What is claimed is:

1. An isolated nucleic acid molecule comprising a nucleotide sequence encoding the amino acid sequence set forth in SEQ ID NO:2 or SEQ ID NO:4.

2. The nucleic acid molecule of claim 1, comprising the coding sequence set forth in SEQ D NO:1 or SEQ D NO:3.

3. The nucleotide sequence contained in *E. coli* strain DH5αpASM deposited as NRRL accession number B-21976.

4. A chimeric construct comprising a heterologous promoter sequence operatively linked to the nucleic acid molecule of claim 1.

5. A recombinant vector comprising the chimeric construct of claim 4.

6. A transgenic plant or bacterial cell comprising the chimeric construct of claim 4.

7. The transgenic host cell according to claim 6, which is a transgenic plant cell.

8. A transgenic plant comprising the transgenic plant cell of claim 7.

9. Transgenic seed from the transgenic plant of claim 8.

10. A chimeric construct comprising a heterologous promoter sequence operatively linked to the nucleic acid molecule of claim 2.

11. A recombinant vector comprising the chimeric construct of claim 10.

12. A transgenic plant or bacterial cell comprising the chimeric construct of claim 10.

13. The transgenic host cell according to claim 12, which is a transgenic plant cell.

14. A transgenic plant comprising the transgenic plant cell of claim 13.

15. Transgenic seed from the transgenic plant of claim 14.

16. A chimeric construct comprising a heterologous promoter sequence operatively linked to the nucleotide sequence of claim 3.

17. A recombinant vector comprising the chimeric construct of claim 16.

18. A transgenic plant or bacterial cell comprising the chimeric construct of claim 16.

19. The transgenic host cell according to claim 18, which is a transgenic plant cell.

20. A transgenic plant comprising the transgenic plant cell of claim 19.

21. Transgenic seed from the transgenic plant of claim 20.

* * * * *

UNITED STATES PATENT AND TRADEMARK OFFICE
CERTIFICATE OF CORRECTION

| | |
|---|---|
| PATENT NO. | : 6,271,445 B1 |
| DATED | : August 7, 2001 |
| INVENTOR(S) | : Ward et al. |

It is certified that error appears in the above-identified patent and that said Letters Patent is hereby corrected as shown below:

<u>Column 1</u>,
Line 6, where it reads "filed May 24, 1998" should read -- filed June 24, 1998 --.

Signed and Sealed this

Thirtieth Day of April, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1172 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 3..1160
      (D) OTHER INFORMATION: /product= "Arabidopsis AIR synthetase c-DNA"

(xi) SEQUENCE DESCRIPTION: SEQ ID NO:1:

```
CC ATG GAA GCT CGG ATT TTG CAG TCT TCT TCT TCC TGT TAT TCG TCT        47
   Met Glu Ala Arg Ile Leu Gln Ser Ser Ser Ser Cys Tyr Ser Ser
    1               5                  10                  15

CTT TAC ACT GTC AAT CGA TCC CGG TTC TCT TCT CCG AAA CCT TTC TCC       95
Leu Tyr Thr Val Asn Arg Ser Arg Phe Ser Ser Pro Lys Pro Phe Ser
                 20                  25                  30

GTC AGC TTT GCT CAG ACG ACG AGA ACA AGG ACT CGT GTA TTA TCC ATG      143
Val Ser Phe Ala Gln Thr Thr Arg Thr Arg Thr Arg Val Leu Ser Met
             35                  40                  45

TCG AAG AAA GAT GGT CGC ACT GAT AAA GAT GAT GAC ACT GAT AGT CTC      191
Ser Lys Lys Asp Gly Arg Thr Asp Lys Asp Asp Asp Thr Asp Ser Leu
         50                  55                  60

AAT TAC AAA GAT TCT GGT GTT GAT ATC GAT GCT GGT GCT GAG CTT GTT      239
Asn Tyr Lys Asp Ser Gly Val Asp Ile Asp Ala Gly Ala Glu Leu Val
     65                  70                  75

AAA CGA ATC GCA AAG ATG GCT CCT GGA ATT GGT GGA TTT GGT GGT CTC      287
Lys Arg Ile Ala Lys Met Ala Pro Gly Ile Gly Gly Phe Gly Gly Leu
 80                  85                  90                  95

TTT CCA TTA GGT GAT AGT TAT CTT GTA GCT GGT ACG GAT GGT GTA GGG      335
Phe Pro Leu Gly Asp Ser Tyr Leu Val Ala Gly Thr Asp Gly Val Gly
                    100                 105                 110

ACT AAA TTG AAA TTG GCA TTT GAA ACT GGA ATT CAT GAC ACC ATT GGA      383
Thr Lys Leu Lys Leu Ala Phe Glu Thr Gly Ile His Asp Thr Ile Gly
                115                 120                 125

ATC GAC TTG GTT GCT ATG AGT GTG AAT GAT ATT ATT ACT TCT GGT GCA      431
Ile Asp Leu Val Ala Met Ser Val Asn Asp Ile Ile Thr Ser Gly Ala
            130                 135                 140
```

```
AAG CCT CTG TTT TTC CTT GAT TAC TTT GCT ACT AGT CGT CTT GAT GTA      479
Lys Pro Leu Phe Phe Leu Asp Tyr Phe Ala Thr Ser Arg Leu Asp Val
    145                 150                 155

GAC CTT GCT GAA AAG GTC ATT AAA GGG ATT GTT GAA GGT TGT CGG CAA      527
Asp Leu Ala Glu Lys Val Ile Lys Gly Ile Val Glu Gly Cys Arg Gln
160                 165                 170                 175

TCG GAA TGT GCT CTC TTA GGG GGA GAG ACT GCA GAG ATG CCT GAC TTT      575
Ser Glu Cys Ala Leu Leu Gly Gly Glu Thr Ala Glu Met Pro Asp Phe
                180                 185                 190

TAT GCA GAG GGC GAG TAC GAT CTA AGT GGG TTT GCA GTA GGC ATA GTA      623
Tyr Ala Glu Gly Glu Tyr Asp Leu Ser Gly Phe Ala Val Gly Ile Val
            195                 200                 205

AAG AAA ACT TCA GTT ATC AAC GGA AAA AAC ATT GTG GCC GGT GAT GTT      671
Lys Lys Thr Ser Val Ile Asn Gly Lys Asn Ile Val Ala Gly Asp Val
        210                 215                 220

CTT ATT GGC CTC CCG TCT AGT GGT GTT CAT TCC AAT GGT TTT TCT CTA      719
Leu Ile Gly Leu Pro Ser Ser Gly Val His Ser Asn Gly Phe Ser Leu
    225                 230                 235

GTA AGA AGG GTA TTG GCT CGA AGC AAT CTT TCG CTG AAT GAT GCG CTT      767
Val Arg Arg Val Leu Ala Arg Ser Asn Leu Ser Leu Asn Asp Ala Leu
240                 245                 250                 255

CCA GGT GGA TCA AGT ACC CTT GGT GAT GCT CTA ATG GCA CCC ACT GTC      815
Pro Gly Gly Ser Ser Thr Leu Gly Asp Ala Leu Met Ala Pro Thr Val
                260                 265                 270

ATT TAC GTG AAA CAG GTA CTT GAT ATG ATA GAA AAA GGA GGA GTG AAA      863
Ile Tyr Val Lys Gln Val Leu Asp Met Ile Glu Lys Gly Gly Val Lys
            275                 280                 285

GGT TTA GCT CAT ATC ACA GGC GGA GGT TTC ACA GAC AAC ATT CCC CGA      911
Gly Leu Ala His Ile Thr Gly Gly Gly Phe Thr Asp Asn Ile Pro Arg
        290                 295                 300

GTC TTC CCG GAC GGT TTG GGT GCT GTT ATT CAC ACC GAT ACT TGG GAA      959
Val Phe Pro Asp Gly Leu Gly Ala Val Ile His Thr Asp Thr Trp Glu
    305                 310                 315

CTT CCA CCG TTG TTC AAG TGG ATT CAA CAG ACT GGG AGA ATA GAA GAC     1007
Leu Pro Pro Leu Phe Lys Trp Ile Gln Gln Thr Gly Arg Ile Glu Asp
320                 325                 330                 335

AGT GAG ATG AGA AGG ACG TTT AAC CTG GGG ATA GGG ATG GTT ATG GTG     1055
Ser Glu Met Arg Arg Thr Phe Asn Leu Gly Ile Gly Met Val Met Val
                340                 345                 350

GTT AGT CCA GAG GCA GCT TCA CGA ATA CTA GAA GAA GTC AAG AAT GGA     1103
Val Ser Pro Glu Ala Ala Ser Arg Ile Leu Glu Glu Val Lys Asn Gly
            355                 360                 365

GAC TAT GTT GCG TAT CGC GTA GGA GAG GTT GTC AAC GGT GAA GGC GTA     1151
Asp Tyr Val Ala Tyr Arg Val Gly Glu Val Val Asn Gly Glu Gly Val
        370                 375                 380

AGC TAT CAG TAGTGAGGAT CC                                           1172
Ser Tyr Gln
    385
```

(2) INFORMATION FOR SEQ ID NO:2:

(i) SEQUENCE CHARACTERISTICS:
        (A) LENGTH: 386 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Ala Arg Ile Leu Gln Ser Ser Ser Ser Cys Tyr Ser Ser Leu
1               5                   10                  15
```

-continued

```
Tyr Thr Val Asn Arg Ser Arg Phe Ser Ser Pro Lys Pro Phe Ser Val
         20                  25                  30

Ser Phe Ala Gln Thr Thr Arg Thr Arg Thr Arg Val Leu Ser Met Ser
         35                  40                  45

Lys Lys Asp Gly Arg Thr Asp Lys Asp Asp Thr Asp Ser Leu Asn
     50                  55                  60

Tyr Lys Asp Ser Gly Val Asp Ile Asp Ala Gly Ala Glu Leu Val Lys
 65                  70                  75                  80

Arg Ile Ala Lys Met Ala Pro Gly Ile Gly Gly Phe Gly Gly Leu Phe
                 85                  90                  95

Pro Leu Gly Asp Ser Tyr Leu Val Ala Gly Thr Asp Gly Val Gly Thr
             100                 105                 110

Lys Leu Lys Leu Ala Phe Glu Thr Gly Ile His Asp Thr Ile Gly Ile
         115                 120                 125

Asp Leu Val Ala Met Ser Val Asn Asp Ile Ile Thr Ser Gly Ala Lys
     130                 135                 140

Pro Leu Phe Phe Leu Asp Tyr Phe Ala Thr Ser Arg Leu Asp Val Asp
145                 150                 155                 160

Leu Ala Glu Lys Val Ile Lys Gly Ile Val Glu Gly Cys Arg Gln Ser
                 165                 170                 175

Glu Cys Ala Leu Leu Gly Gly Glu Thr Ala Glu Met Pro Asp Phe Tyr
             180                 185                 190

Ala Glu Gly Glu Tyr Asp Leu Ser Gly Phe Ala Val Gly Ile Val Lys
         195                 200                 205

Lys Thr Ser Val Ile Asn Gly Lys Asn Ile Val Ala Gly Asp Val Leu
     210                 215                 220

Ile Gly Leu Pro Ser Ser Gly Val His Ser Asn Gly Phe Ser Leu Val
225                 230                 235                 240

Arg Arg Val Leu Ala Arg Ser Asn Leu Ser Leu Asn Asp Ala Leu Pro
                 245                 250                 255

Gly Gly Ser Ser Thr Leu Gly Asp Ala Leu Met Ala Pro Thr Val Ile
             260                 265                 270

Tyr Val Lys Gln Val Leu Asp Met Ile Glu Lys Gly Gly Val Lys Gly
         275                 280                 285

Leu Ala His Ile Thr Gly Gly Gly Phe Thr Asp Asn Ile Pro Arg Val
     290                 295                 300

Phe Pro Asp Gly Leu Gly Ala Val Ile His Thr Asp Thr Trp Glu Leu
305                 310                 315                 320

Pro Pro Leu Phe Lys Trp Ile Gln Gln Thr Gly Arg Ile Glu Asp Ser
                 325                 330                 335

Glu Met Arg Arg Thr Phe Asn Leu Gly Ile Gly Met Val Met Val Val
             340                 345                 350

Ser Pro Glu Ala Ala Ser Arg Ile Leu Glu Glu Val Lys Asn Gly Asp
         355                 360                 365

Tyr Val Ala Tyr Arg Val Gly Glu Val Val Asn Gly Glu Gly Val Ser
     370                 375                 380

Tyr Gln
385
```

(2) INFORMATION FOR SEQ ID NO:3:

(i) SEQUENCE CHARACTERISTICS:
        (A) LENGTH: 1013 base pairs
        (B) TYPE: nucleic acid
        (C) STRANDEDNESS: single

```
            (D) TOPOLOGY: linear (ii) MOLECULE TYPE: cDNA (iii) HYPOTHETICAL: NO (ix) FEATURE:
            (A) NAME/KEY: mat_peptide
            (B) LOCATION: 3..1001
            (D) OTHER INFORMATION: /product= "coding sequence of
                Arabidopsis AIR synthetase putative mature protein"

(ix) FEATURE:
            (A) NAME/KEY: CDS
            (B) LOCATION: 3..1001

(xi) SEQUENCE DESCRIPTION: SEQ ID NO:3:

CC ATG GAT AAA GAT GAT GAC ACT GAT AGT CTC AAT TAC AAA GAT TCT      47
   Met Asp Lys Asp Asp Asp Thr Asp Ser Leu Asn Tyr Lys Asp Ser
   1               5                   10                  15

GGT GTT GAT ATC GAT GCT GGT GCT GAG CTT GTT AAA CGA ATC GCA AAG     95
Gly Val Asp Ile Asp Ala Gly Ala Glu Leu Val Lys Arg Ile Ala Lys
                20                  25                  30

ATG GCT CCT GGA ATT GGT GGA TTT GGT GGT CTC TTT CCA TTA GGT GAT    143
Met Ala Pro Gly Ile Gly Gly Phe Gly Gly Leu Phe Pro Leu Gly Asp
            35                  40                  45

AGT TAT CTT GTA GCT GGT ACG GAT GGT GTA GGG ACT AAA TTG AAA TTG    191
Ser Tyr Leu Val Ala Gly Thr Asp Gly Val Gly Thr Lys Leu Lys Leu
        50                  55                  60

GCA TTT GAA ACT GGA ATT CAT GAC ACC ATT GGA ATC GAC TTG GTT GCT    239
Ala Phe Glu Thr Gly Ile His Asp Thr Ile Gly Ile Asp Leu Val Ala
65                  70                  75

ATG AGT GTG AAT GAT ATT ATT ACT TCT GGT GCA AAG CCT CTG TTT TTC    287
Met Ser Val Asn Asp Ile Ile Thr Ser Gly Ala Lys Pro Leu Phe Phe
80                  85                  90                  95

CTT GAT TAC TTT GCT ACT AGT CGT CTT GAT GTA GAC CTT GCT GAA AAG    335
Leu Asp Tyr Phe Ala Thr Ser Arg Leu Asp Val Asp Leu Ala Glu Lys
                100                 105                 110

GTC ATT AAA GGG ATT GTT GAA GGT TGT CGG CAA TCG GAA TGT GCT CTC    383
Val Ile Lys Gly Ile Val Glu Gly Cys Arg Gln Ser Glu Cys Ala Leu
            115                 120                 125

TTA GGG GGA GAG ACT GCA GAG ATG CCT GAC TTT TAT GCA GAG GGC GAG    431
Leu Gly Gly Glu Thr Ala Glu Met Pro Asp Phe Tyr Ala Glu Gly Glu
        130                 135                 140

TAC GAT CTA AGT GGG TTT GCA GTA GGC ATA GTA AAG AAA ACT TCA GTT    479
Tyr Asp Leu Ser Gly Phe Ala Val Gly Ile Val Lys Lys Thr Ser Val
    145                 150                 155

ATC AAC GGA AAA AAC ATT GTG GCC GGT GAT GTT CTT ATT GGC CTC CCG    527
Ile Asn Gly Lys Asn Ile Val Ala Gly Asp Val Leu Ile Gly Leu Pro
160                 165                 170                 175

TCT AGT GGT GTT CAT TCC AAT GGT TTT TCT CTA GTA AGA AGG GTA TTG    575
Ser Ser Gly Val His Ser Asn Gly Phe Ser Leu Val Arg Arg Val Leu
                180                 185                 190

GCT CGA AGC AAT CTT TCG CTG AAT GAT GCG CTT CCA GGT GGA TCA AGT    623
Ala Arg Ser Asn Leu Ser Leu Asn Asp Ala Leu Pro Gly Gly Ser Ser
            195                 200                 205

ACC CTT GGT GAT GCT CTA ATG GCA CCC ACT GTC ATT TAC GTG AAA CAG    671
Thr Leu Gly Asp Ala Leu Met Ala Pro Thr Val Ile Tyr Val Lys Gln
        210                 215                 220

GTA CTT GAT ATG ATA GAA AAA GGA GGA GTG AAA GGT TTA GCT CAT ATC    719
Val Leu Asp Met Ile Glu Lys Gly Gly Val Lys Gly Leu Ala His Ile
    225                 230                 235

ACA GGC GGA GGT TTC ACA GAC AAC ATT CCC CGA GTC TTC CCG GAC GGT    767
```

-continued

```
                    Thr Gly Gly Phe Thr Asp Asn Ile Pro Arg Val Phe Pro Asp Gly
                    240                 245                 250                 255

TTG GGT GCT GTT ATT CAC ACC GAT ACT TGG GAA CTT CCA CCG TTG TTC        815
Leu Gly Ala Val Ile His Thr Asp Thr Trp Glu Leu Pro Pro Leu Phe
                260                 265                 270

AAG TGG ATT CAA CAG ACT GGG AGA ATA GAA GAC AGT GAG ATG AGA AGG        863
Lys Trp Ile Gln Gln Thr Gly Arg Ile Glu Asp Ser Glu Met Arg Arg
            275                 280                 285

ACG TTT AAC CTG GGG ATA GGG ATG GTT ATG GTG GTT AGT CCA GAG GCA        911
Thr Phe Asn Leu Gly Ile Gly Met Val Met Val Val Ser Pro Glu Ala
            290                 295                 300

GCT TCA CGA ATA CTA GAA GAA GTC AAG AAT GGA GAC TAT GTT GCG TAT        959
Ala Ser Arg Ile Leu Glu Glu Val Lys Asn Gly Asp Tyr Val Ala Tyr
        305                 310                 315

CGC GTA GGA GAG GTT GTC AAC GGT GAA GGC GTA AGC TAT CAG                1001
Arg Val Gly Glu Val Val Asn Gly Glu Gly Val Ser Tyr Gln
320                 325                 330

TAGTGAGGAT CC                                                          1013
```

(2) INFORMATION FOR SEQ ID NO:4:

(i) SEQUENCE CHARACTERISTICS:
        (A) LENGTH: 333 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Lys Asp Asp Thr Asp Ser Leu Asn Tyr Lys Asp Ser Gly
1               5                   10                  15

Val Asp Ile Asp Ala Gly Ala Glu Leu Val Lys Arg Ile Ala Lys Met
                20                  25                  30

Ala Pro Gly Ile Gly Phe Gly Gly Leu Phe Pro Leu Gly Asp Ser
            35                  40                  45

Tyr Leu Val Ala Gly Thr Asp Gly Val Gly Thr Lys Leu Lys Leu Ala
    50                  55                  60

Phe Glu Thr Gly Ile His Asp Thr Ile Gly Ile Asp Leu Val Ala Met
65                  70                  75                  80

Ser Val Asn Asp Ile Ile Thr Ser Gly Ala Lys Pro Leu Phe Phe Leu
                85                  90                  95

Asp Tyr Phe Ala Thr Ser Arg Leu Asp Val Asp Leu Ala Glu Lys Val
            100                 105                 110

Ile Lys Gly Ile Val Glu Gly Cys Arg Gln Ser Glu Cys Ala Leu Leu
        115                 120                 125

Gly Gly Glu Thr Ala Glu Met Pro Asp Phe Tyr Ala Glu Gly Glu Tyr
    130                 135                 140

Asp Leu Ser Gly Phe Ala Val Gly Ile Val Lys Lys Thr Ser Val Ile
145                 150                 155                 160

Asn Gly Lys Asn Ile Val Ala Gly Asp Val Leu Ile Gly Leu Pro Ser
                165                 170                 175

Ser Gly Val His Ser Asn Gly Phe Ser Leu Val Arg Arg Val Leu Ala
            180                 185                 190

Arg Ser Asn Leu Ser Leu Asn Asp Ala Leu Pro Gly Gly Ser Ser Thr
        195                 200                 205

Leu Gly Asp Ala Leu Met Ala Pro Thr Val Ile Tyr Val Lys Gln Val
    210                 215                 220
```

```
Leu Asp Met Ile Glu Lys Gly Val Lys Gly Leu Ala His Ile Thr
225                 230                 235                 240

Gly Gly Gly Phe Thr Asp Asn Ile Pro Arg Val Phe Pro Asp Gly Leu
                245                 250                 255

Gly Ala Val Ile His Thr Asp Thr Trp Glu Leu Pro Pro Leu Phe Lys
                260                 265                 270

Trp Ile Gln Gln Thr Gly Arg Ile Glu Asp Ser Glu Met Arg Arg Thr
                275                 280                 285

Phe Asn Leu Gly Ile Gly Met Val Met Val Val Ser Pro Glu Ala Ala
                290                 295                 300

Ser Arg Ile Leu Glu Glu Val Lys Asn Gly Asp Tyr Val Ala Tyr Arg
305                 310                 315                 320

Val Gly Glu Val Val Asn Gly Glu Gly Val Ser Tyr Gln
                325                 330
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:5:

GTACCTCGAG TCTAGACTCG AG                                          22

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:6:

GATCGAGCTC GTTCTCTTCT GTGTCATC                              28

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:7:

GATCCCATGG TCCCCAGGTA AAGACGTC                              28

(2) INFORMATION FOR SEQ ID NO:8:

(i) SEQUENCE CHARACTERISTICS:

-continued (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:8:

CGCGGATCCT CACTACTGAT AGCTTACGCC TTCACC                                  36

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:9:

TTGAAGCCAT GGAAGCTCGG ATTTTG                                             26

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:10:

CGCATGCCAT GGATAAAGAT GATGACACTG ATAGTCT                                 37